US 7,112,577 B2

(12) United States Patent
Hamied et al.

(10) Patent No.: US 7,112,577 B2
(45) Date of Patent: Sep. 26, 2006

(54) PHARMACEUTICALLY ACCEPTABLE ALENDRONATE SALTS IN AMORPHOUS FORM

(75) Inventors: Yusuf Khwaja Hamied, Mumbai (IN); Dharmaraj Ramachandra Rao, Maharashtra (IN); Rajendra Narayanrao Kankan, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 10/492,977

(22) PCT Filed: Oct. 18, 2002

(86) PCT No.: PCT/GB02/04730

§ 371 (c)(1),
(2), (4) Date: Jul. 26, 2004

(87) PCT Pub. No.: WO03/033508

PCT Pub. Date: Apr. 24, 2003

(65) Prior Publication Data

US 2004/0259846 A1    Dec. 23, 2004

(30) Foreign Application Priority Data

Oct. 18, 2001    (GB) ................. 0125081.0

(51) Int. Cl.
*A01N 57/00*    (2006.01)
*A61K 31/66*    (2006.01)

(52) U.S. Cl. .................... 514/102; 652/13; 652/21
(58) Field of Classification Search ................ 514/102; 562/21
See application file for complete search history.

(56) References Cited

U.S. PATENT DOCUMENTS

| 4,304,734 A | * | 12/1981 | Jary et al. ................ 562/13 |
| 4,922,007 A | * | 5/1990 | Kieczykowski et al. ...... 562/13 |
| 6,268,524 B1 | * | 7/2001 | Shinal ................ 562/13 |

FOREIGN PATENT DOCUMENTS

| EP | 0402152 | 12/1990 |
| WO | 9639149 | 12/1996 |
| WO | 0012517 | 3/2000 |
| WO | 0034293 | 6/2000 |
| WO | 0130788 | 5/2001 |
| WO | WO 01/30788 A1 * | 5/2001 |

* cited by examiner

*Primary Examiner*—Thurman K. Page
*Assistant Examiner*—Chukwuma Nwaonicha
(74) *Attorney, Agent, or Firm*—Stevens, Davis, Miller & Mosher, L.L.P.

(57) ABSTRACT

A pharmaceutically acceptable alendronate salt in an amorphous form.

14 Claims, 1 Drawing Sheet

PHARMACEUTICALLY ACCEPTABLE ALENDRONATE SALTS IN AMORPHOUS FORM

Figure 1:
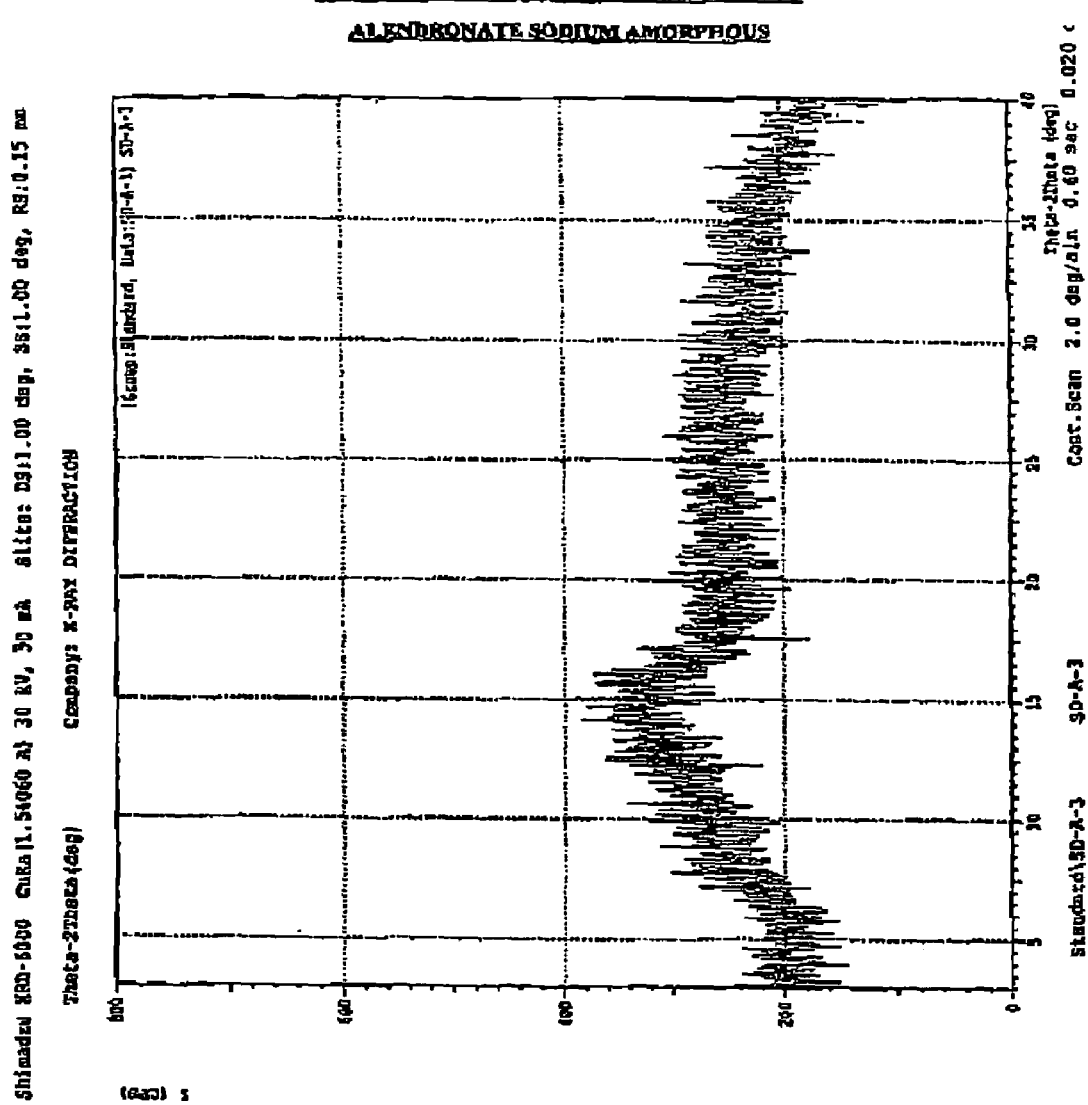

This application is a §371 Application of International Application No. PCT/GB02/04730, filed on Oct. 18, 2002, claiming the priority of Great Britain Application No. 0125081.0, filed Oct. 18, 2001, the entire disclosures of which are incorporated herein by reference in their entireties.

This invention relates to pharmaceutically acceptable salts of 4-amino-1-hydroxybutylidene bisphosphonic acid (alendronate salts) in amorphous form and a process of preparing the same.

Alendronate sodium is an inhibitor of bone resorbtion useful for the treatment of diseases such as Paget's disease and osteoporosis.

Processes used heretofore for the production of alendronate sodium result in a crystalline product EP 402152 discloses the preparation of alendronate monosodium trihydrate which is crystalline. EP 462663 discloses an improved process for making alendronate and crystalline salts thereof which process avoids the use of a strongly acidic hydrolysis medium. A pharmaceutical composition comprising the anhydrous crystalline form of alendronate sodium is disclosed in WO 96139149.

In order to facilitate easy formulation into pharmaceutical compositions, high solubility of an alendronate salt, such as alendronate sodium, is desired. High solubility may also be a desirable characteristic in terms of the pharmacological properties of this compound.

The preset invention is based on the discovery that pharmaceutically acceptable alendronate salts in an amorphous form are non-hygroscopic and exhibit surprisingly better solubility characteristics as compared to, for example, crystalline alendronate sodium trihydrate. In particular, an alendronate salt in an amorphous form of the present invention dissolves in water at a faster rate than the crystalline material.

There is provided by the present invention, therefore, a pharmaceutically acceptable alendronate salt in an amorphous form. In particular, the present invention is concerned with a monovalent pharmaceutically acceptable alendronate salt in an amorphous form. More particularly, the present invention provides alendronate monosodium in an amorphous form.

The term "amorphous" as used herein denotes a physical state which is not crystalline and may be verified by x-ray diffraction and other means including but not limited to observation with a polarized light microscope and differential scanning calorimetry. More particularly, an amorphous alendronate salt in accordance with the present invention is preferably essentially free from any crystalline form of alendronate salts.

The present invention provides a pharmaceutically acceptable alendronate salt in an amorphous form, preferably containing less than about 3%, and most preferably less than about 1%, water. In particular, the present invention is concerned with a monovalent pharmaceutically acceptable alendronate salt in an amorphous form, preferably containing less than about 3%, and most preferably less than about 1%, water. More particularly, the present invention provides alendronate monosodium in an amorphous form, preferably containing less than about 3%, and most preferably less than about 1%, water.

The present invention also provides amorphous alendronate monosodium having an X-ray diffraction pattern as shown in the accompanying Figure.

The invention also includes a pharmaceutical composition comprising a therapeutically effective amount of a pharmaceutically acceptable alendronate salt in an amorphous form (in particular alendronate monosodium in an amorphous form), together with a pharmaceutically acceptable carrier, diluent or excipient therefor.

The invention also provides a method of inhibiting bone resorption in a patient, which method comprises administering to a patient suffering from or susceptible to bone resorption a therapeutically effective amount of a pharmaceutically acceptable alendronate salt in an amorphous form substantially as herein before described in particular alendronate monosodium in an amorphous form substantially as herein before described, or a pharmaceutical composition comprising the same substantially as hereinbefore described.

The term "inhibition of bone resorption" as used herein, refers to treatment and prevention of bone loss, especially inhibiting the removal of existing bone, for example through direct or indirect alteration of osteoclast formation or activity. Thus a pharmaceutically acceptable alendronate salt in an amorphous form according to the present invention can, for example, prevent bone loss by the direct or indirect alteration of osteoclast formation or activity and which may increase bone mass in patient treatment populations.

Such methods of treatment according to the present invention are useful in treating bone fractures, defects and disorders which can result from the pathological conditions of osteoporosis, osteoarthritis, Paget's disease, osteohalisteresis, osteomalacia, bone loss resulting from multiple myeloma and other forms of related cancer, bone loss resulting from side effects of disuse, other medical treatment (such as steroids), rheumatoid-related and age-related loss of bone mass and the like. Methods according to the present invention may have particular utility for the treatment of female patients who are post-menopausal.

The term "treating" or "inhibiting" as used herein with respect to methods of the present invention shall mean providing a patient with an amount of a pharmaceutically acceptable alendronate salt in an amorphous form sufficient to act prophylactically with respect to a disease state substantially as herein before described associated with bone resorption in the patient, and/or providing a patient with an amount of a pharmaceutically acceptable alendronate salt in an amorphous form sufficient to alleviate or substantially eliminate a disease state substantially as herein before described associated with bone resorption in the patient.

In another aspect, the invention provides a process for the production of a pharmaceutically acceptable alendronate salt in an amorphous form (in particular alendronate monosodium in an amorphous form), which process comprises removing solvent from a solution of an alendronate salt, so as to obtain an amorphous product according to the present invention.

In the process of the invention, solvent is removed from the solution of an alendronate salt therein, to form amorphous alendronate according to the present invention. The preferred solvent is water since pharmaceutically acceptable alendronate salts in an amorphous form are not very soluble in other common solvents. In principle, however, any solvent can be used.

The solution of an alendronate salt should be essentially free of any crystalline alendronate salt. The solution can, however, contain some (non-crystalline) suspended alendronate salt so as to form a cloudy solution, although this is not preferred.

The solution of an alendronate salt can be made in any suitable way. For example, it can be prepared by dissolving sodium alendronate, eg trihydrate or anhydrous product, in a solvent. The mixture can be heated to aid in the dissolution: in the case of an aqueous solution, we have found it can be advantageous to heat to about 50° C. to 60° C.

Alternatively, an alendronate salt can be formed in situ in the solvent. One example of this is to add sodium hydroxide solution to a suspension of alendronic acid in water to form the alendronate soon in solution in water. Most preferably, the volume of alendronic acid is suspended in about 30 volumes of water and then the pH is adjusted to about 4.3 to 4.4 with sodium hydroxide.

The solution of an alendronate salt used in the process of the invention will preferably have a volume ratio of an alendronate salt to solvent of about 1:10 to about 1:30 or more, depending on the solubility in the solvent used. For aqueous solutions, a ratio of about 1:10 is preferred. In general, the less solvent there is present, the less needs to be removed to form the amorphous product, so lower solvent qualities are preferred for this reason.

The removal of solvent can be effected by any suitable means appropriate to the solvent in question, from simple evaporation to more intensive procedures. In the most usual case of aqueous solutions, we prefer to use spray drying. In spray drying aqueous solutions, the inlet temperature is preferably from 120° C. to 250° C., the outlet tempers preferably firm 70° C. to 120° C. and the feed rate preferably from 5 to 25 ml/min. However, other temperatures and rates can be used.

The product can be characterised by powder X-ray crylstallography. Amorphous alendronate sodium is characterised by the absence of a well defined diffractogram. A typical diffactogram is shown in the accompanying FIG. 1. When observed under a microscope, the amorphous product of the invention is seen as spherical beads whereas, in contrast, crystalline material exhibits rhombic structure. The moisture content if amorphous aldenronate sodium of the invention preferably no greater than about 3% by weight, more preferably less than about 1%. At these moisture contents, the amorphous product is stable.

The following Examples illustrate the process of the invention.

PREPARATION OF ALENDRONATE SODIUM AMORPHOUS

EXAMPLE 1

Alendronate sodium trihydrate 25 g in 250 ml of water was heated at 60° C. to obtain a clear solution. This solution was spray dried in a Lab Plant Spray Drier SD 05 with an inlet temperature of 200° C., outlet temperature of 100° C., compressed air rate of 0.3 m$^3$/hr and a feed rate of 15 ml/min, to obtain 20 g of the product The amorphous product was characterised by powder X-ray diffraction.

Moisture content: less than 1%.

EXAMPLE 2

Crystalline alendronate sodium anhydrous 25 g in 500 ml of water was heated at 50° C. to obtain an almost clear solution. This solution was spray dried in a Lab Plant Spray Drier SD 05 with an inlet temperature of 160° C., outlet temperature of 80° C., compressed air rate of 0.3 m$^3$/hr and a feed rate of 8 ml/min, to obtain 18 g of the product.

The amorphous product was characterised by powder X-ray diffraction.

EXAMPLE 3

To a suspension of alendronic acid 25 g in 750 ml of water was added a 20% solution of sodium hydroxide and pH adjusted to 4.3 to 4.4 to obtain a clear solution. This solution was spray dried in a Lab Plant Spray Drier SD 05 with an inlet temperature of 180° C., outlet temperature of 90° C., compressed air rate of 0.3 m$^3$/hr and a feed rate of 10 ml/min, to obtain 20 g of the product.

The amorphous product was characterised by powder X-ray diffraction.

According to another aspect of the invention, the amorphous alendronate sodium can be formulated into pharmaceutical compositions, for example in the form of tablets (coated or uncoated) or capsules for oral administration. Suitable carriers include, for example sugars, starch and derivatives, cellulose and derivatives, gums and polyalcohols. The compositions may also contain additional ingredients such as lubricants, compression aids, flavours, sweeteners and preservatives.

The invention claimed is:

1. Alendronate monosodium in amorphous form.

2. Alendronate monosodium in amorphous form, containing less than about 3% water.

3. Alendronate monosodium in amorphous form according to claim 2, containing less than about 1% water.

4. Alendronate monosodium in amorphous form, having an X-ray diffraction pattern as shown in FIG. 1.

5. A process for the production of alendronate monosodium in amorphous form according to claim 1, which process comprises removing a solvent from a solution of alendronate monosodium by spray drying, so as to obtain alendronate monosodium in amorphous form.

6. A process according to claim 5, wherein the solvent comprises water.

7. A process according to claim 6, wherein said solution is produced by suspending alendronic acid in water and adjusting the pH using aqueous sodium hydroxide.

8. A pharmaceutical composition comprising a therapeutically effective amount of alendronate monosodium in amorphous form according to claim 1, together with a pharmaceutically acceptable carrier, diluent or excipient therefor.

9. A method of inhibiting bone resorption in a patient, which method comprises administering to a patient suffering from or susceptible to bone resorption a therapeutically effective amount of alendronate monosodium in amorphous form according to claim 1.

10. A method according to claim 9, for the treatment of fractures, disorders which result from osteoporosis, osteoarthritis, Paget's disease, osteohalisteresis, osteomalacia, bone loss resulting from multiple myeloma and other forms of related cancer, bone loss resulting from side effects of disuse, steroid treatment, rheumatoid-related and age-related loss of bone mass.

11. A method of inhibiting bone resorption in a patient, which method comprises administering to a patient suffering from or susceptible to bone resorption a therapeutically effective amount of alendronate monosodium in amorphous form according to claim 2.

12. A method of inhibiting bone resorption in a patient, which method comprises administering to a patient suffering from or susceptible to bone resorption a therapeutically effective amount of alendronate monosodium in amorphous form according to claim 3.

13. A method of inhibiting bone resorption in a patient, which method comprises administering to a patient suffering from or susceptible to bone resorption a therapeutically effective amount of alendronate monosodium in amorphous form according to claim 4.

14. A method of inhibiting bone resorption in a patient, which method comprises administering to a patient suffering from or susceptible to bone resorption a therapeutically effective amount of a pharmaceutical composition according to claim 8.

* * * * *